(12) United States Patent
Sanborn

(10) Patent No.: US 10,192,027 B2
(45) Date of Patent: Jan. 29, 2019

(54) SYSTEMS AND METHODS FOR RNA ANALYSIS IN FUNCTIONAL CONFIRMATION OF CANCER MUTATIONS

(71) Applicant: Five3 Genomics, LLC, Santa Cruz, CA (US)

(72) Inventor: John Zachary Sanborn, Santa Cruz, CA (US)

(73) Assignee: FIVE3 GENOMICS, LLC, Santa Cruz, CA (US)

( * ) Notice: Subject to any disclaimer, the term of this patent is extended or adjusted under 35 U.S.C. 154(b) by 753 days.

(21) Appl. No.: 14/668,518

(22) Filed: Mar. 25, 2015

(65) Prior Publication Data

US 2015/0278435 A1    Oct. 1, 2015

Related U.S. Application Data

(60) Provisional application No. 61/970,054, filed on Mar. 25, 2014.

(51) Int. Cl.
G06F 19/18 (2011.01)
G06F 19/22 (2011.01)
G06F 19/28 (2011.01)

(52) U.S. Cl.
CPC .............. *G06F 19/18* (2013.01); *G06F 19/22* (2013.01); *G06F 19/28* (2013.01)

(58) Field of Classification Search
None
See application file for complete search history.

(56) References Cited

U.S. PATENT DOCUMENTS

| 2004/0248251 A1 | 12/2004 | Lal et al. |
| 2010/0292930 A1 | 11/2010 | Koster et al. |
| 2012/0059670 A1 | 3/2012 | Sanborn et al. |
| 2012/0066001 A1 | 3/2012 | Sanborn et al. |
| 2013/0332081 A1 | 12/2013 | Reese et al. |

FOREIGN PATENT DOCUMENTS

| CA | 2387035 | 4/2001 |
| CN | 1920054 | 2/2007 |
| WO | 2003023404 | 3/2003 |
| WO | 2003027228 | 4/2003 |
| WO | 2007149062 | 12/2007 |
| WO | WO2011/139345 A2 | 11/2011 |
| WO | 2012-106559 A1 | 8/2012 |
| WO | 2012106559 | 8/2012 |
| WO | WO2013/062505 A1 | 5/2013 |
| WO | 2013-113921 A1 | 8/2013 |
| WO | 2013113921 | 8/2013 |

OTHER PUBLICATIONS

Stenson et al. The Human Gene Mutation Database: 2008 update Genome Medicine vol. 1, article 13 (Year: 2009).*
ISA/KR, International Search Report and Written Opinion, PCT/US2015/022521, dated Jun. 9, 2015, 10 pages.
He et al., "A Global View of Cancer-Specific Transcript Variants by Subtractive Transcriptome-Wide Analysis", PLoS One | www.plosone.org, Mar. 2009 | vol. 4 | Issue 3 | e4732.

* cited by examiner

*Primary Examiner* — John S Brusca

(74) *Attorney, Agent, or Firm* — Umberg Zipser, LLP

(57) ABSTRACT

Contemplated systems and methods integrate genomic/exomic data with transcriptomic data by correlating a cancer associated mutation in the genome/exome with the transcription level of the affected gene carrying the mutation, particularly where the mutation is a 3-terminal nonsense mutation.

8 Claims, 17 Drawing Sheets

US 10,192,027 B2

SYSTEMS AND METHODS FOR RNA ANALYSIS IN FUNCTIONAL CONFIRMATION OF CANCER MUTATIONS

This application claims the benefit of priority to U.S. provisional application 61/970,054 filed on Mar. 25, 2014. This and all other extrinsic references cited herein are incorporated by reference in their entirety. Also, where a definition or use of a term in an incorporated reference is inconsistent or contrary to the definition of that term provided herein, the definition of that term provided herein applies and the definition of that term in the reference does not apply.

FIELD OF THE INVENTION

The field of the invention is omics analysis, and especially as it relates to RNomics in cancer diagnosis and therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

With the advent of affordable and relatively fast whole genome sequencing, significant quantities of detailed knowledge on the DNA level have become available. However, meaningful analysis of the data has been impeded in most cases by the sheer volume of information and lack of infrastructure and computing algorithms. Such difficulties are further compounded where additional omics information is available for analysis, and especially RNomics and proteomics on a tissue and even cellular level. Thus, integration of such additional data has become a rate-limiting step in many prognostic, diagnostic, and therapeutic approaches.

More recently, and as for example described in US 2012/0059670 and US 2012/0066001, high throughput sequence analysis for genomics data has become substantially more efficient by incremental differential alignment and comparison of a patient's tumor and matched healthy tissue. Such information can then be further analyzed using a pathway recognition algorithm as also previously described in WO/2011/139345 and WO/2013/062505. However, even with these advanced tools, presence of a particular constellation of mutations in a tumor genome does not necessarily predict that the mutated gene is actually expressed, and if so, what effect the mutation might have. While findings per se from RNomics may be helpful, such results in isolation will typically not be of high informative value without contextual additional data from genomics and proteomics.

Thus, even though numerous systems and methods for analyzing omics data are known in the art, there is still a need to improve omics analysis and integration of information gleaned from various omics platforms.

SUMMARY OF THE INVENTION

The present inventive subject matter is drawn to systems and methods of integrating RNomics information with various analytic systems, and especially genomics analysis, and identification of various markers for neoplastic diseases. More specifically, the inventors have discovered that patient and tumor specific mutations on the genome or exome level can be contextualized with analysis of the transcription levels for the corresponding RNA, especially where the mutations are nonsense mutations in selected genes having a known association with malignancies.

In one aspect of the inventive subject matter, a method of processing omics data that includes a step of informationally coupling a database with an analysis engine, wherein the database stores a genomic data set and a transcriptomic data set. In generally contemplated methods, the genomic data set is representative of a mutation in at least one gene of a diseased tissue (e.g., cancerous tissue) of a patient, wherein the mutation is relative to a normal tissue of the patient, and the transcriptomic data set is representative of the mutation in and expression level of the at least one gene of the diseased tissue of the patient, wherein the mutation and expression level are relative to the normal tissue of the patient. In another step of contemplated methods, the sequence analysis engine is used to associate the transcriptomic data set with the genomic data set using the mutation (e.g., when the mutation is in the same position), and to identify the mutation as a nonsense mutation. Upon identification of the mutation as nonsense mutation the sequence analysis engine is further used to identify a position of the mutation within the 3'-end portion of the at least one gene, and to identify the expression level of the at least one gene. In still another step of contemplated methods, the analysis engine updates or generates an omics record in an omics database using the position of the mutation and the expression level.

While not limiting to the inventive subject matter, further contemplated methods may include a step of informationally coupling a sequence database or sequencing device with the sequence analysis engine, and another step of using the sequence analysis engine to generate the transcriptomic data set and the genomic data set. Most typically, but not necessarily, the transcriptomic data set and the genomic data set are differential sequence objects. It is further generally contemplated that the transcriptomic data are obtained from cDNA or polyA$^+$RNA.

In another aspect of contemplated methods, the omics record will be updated when the identified position is in a position in the 3-terminal portion of the gene (e.g., terminal 3 exons, terminal 2 exons) and/or when the identified expression level is above an expression level relative to the normal tissue. Among other genes that are contemplated, exemplary suitable genes include CDKN2A, ARID1A, FAT1, TP53, PTEN, AHNAK, SRRM2, RASA1, PIK3R1, and MRPL32.

Therefore, and viewed from another perspective, an omics record computer system will include at least one processor and at least one memory coupled with the processor and configured to store (1) a genomic data set representative of a mutation in at least one gene of a diseased tissue of a patient, wherein the mutation is relative to a normal tissue of the patient, and (2) a transcriptomic data set representative of the mutation in and expression level of the at least one gene of the diseased tissue of the patient, wherein the mutation and expression level are relative to the normal tissue of the patient. Contemplated systems will further comprise an analysis engine that is informationally coupled to an omics database, and that is executable on the at last one processor according to software instructions stored in the at least one memory and that configures the processor to (a) associate the genomic data set and the transcriptomic data set using the mutation; (b) identify the mutation as a nonsense mutation, and upon identification of the mutation as nonsense mutation: identify a position of the mutation within the 3'-end portion of the at least one gene; and identify the expression level of the at least one gene; (c) use the identified position and expression level to update an omics record in the omics data base.

In further aspects of contemplated computer systems, at least one of the transcriptomic data set and the genomic data set are differential sequence objects, and/or the diseased tissue is a cancerous tissue. Most typically, the transcriptomic data set is based on analysis of polyA$^+$RNA or cDNA. As already noted above, the omics record can be updated when the identified position is a position in the 3-terminal portion of the gene and/or when the identified expression level is above an expression level relative to the normal tissue.

It is also contemplated that the gene is a cancer-associated gene, for example, CDKN2A, ARID1A, FAT1, TP53, PTEN, AHNAK, SRRM2, RASA1, PIK3R1, and/or MRPL32. Therefore, the omics record may be updated to confirm a diagnosis (e.g., of a neoplastic disease) or suggest a therapeutic option (e.g., for the neoplastic disease).

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
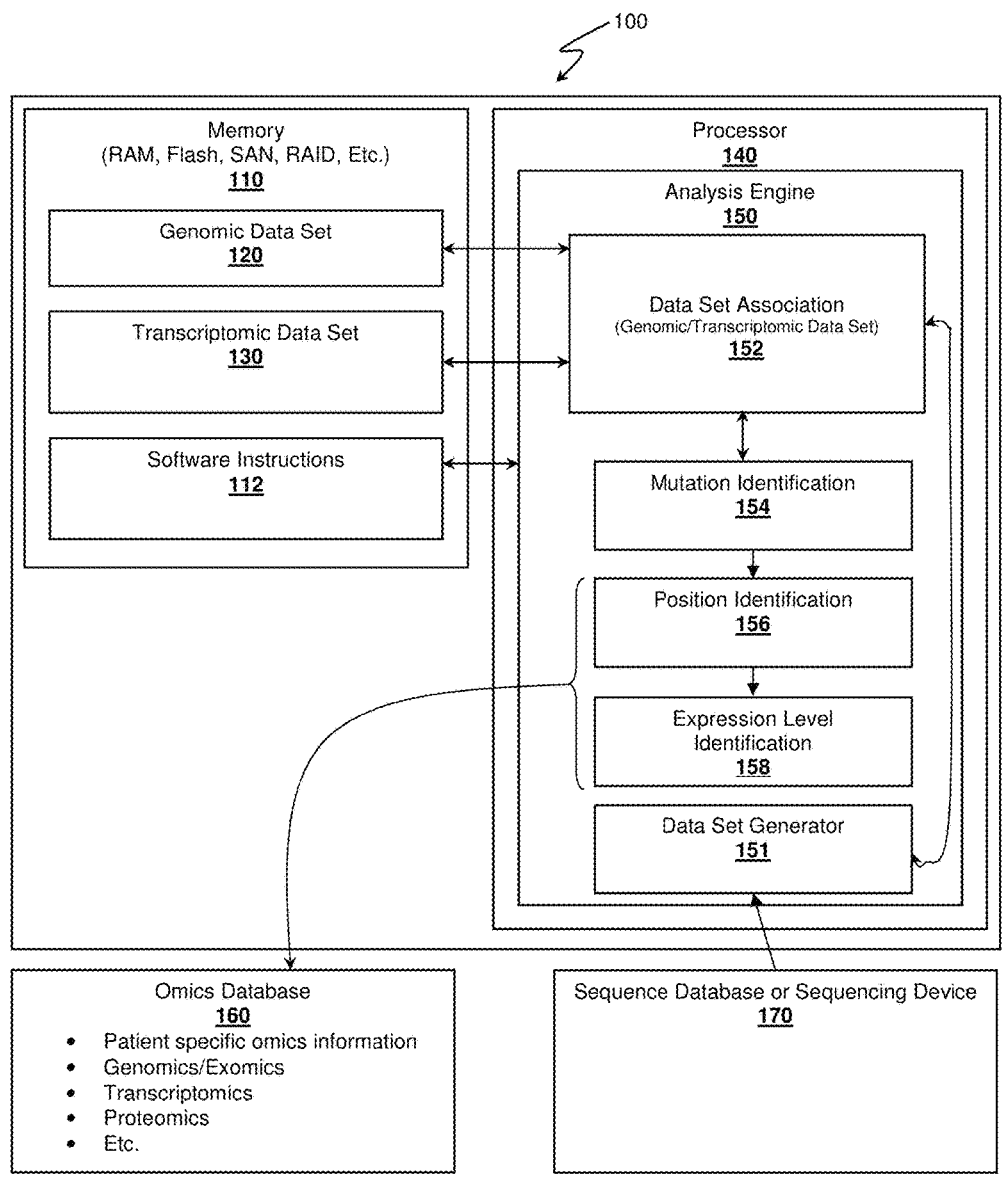
FIG. 1 is an exemplary schematic of an omics record computer system according to the inventive subject matter.

The inventors have discovered that genomic mutations in cancer tissues are not equally transcribed into RNA, but that selected mutation types in cancer associated genes, and especially nonsense mutations are transcribed at a higher rate, particularly where the mutation is located in a 3-terminal portion of the cancer associated gene. Even more notably, such highly transcribed genes were found to be involved in more than one cancer type. Consequently, the inventors contemplate systems and methods of detecting molecular markers for diagnosis and treatment of various cancers based on integration of genomic and transcriptomic information. Viewed from another perspective, patient specific highly transcribed mutated RNA (and especially nonsense mutated RNA) may be identified and/or used as a diagnostic tool for the presence, treatment, and/or prevention of various cancers. To that end, various methods of processing omics data and omics record computer systems are contemplated and discussed in more detail below.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or otherwise program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions or operate on target data or data objects stored in the memory.

For example, one contemplated implementation of an omics record computer system and method of processing omics data is shown in FIG. 1. Here, omics record computer system 100 comprises memory 110 and processor 140 coupled to the memory. Stored in memory 110 is genomic data set 120 and transcriptomic data set 130. Alternatively, or additionally, the genomic and/or transcriptome data set may also be provided from a data set generator 151 of analysis engine 150. In such case, raw sequence data can be provided from a sequence database and/or a sequencing device 170 that produces omic data. Regardless of the source of the genomic data set 120 and transcriptome data set 130 it is contemplated that software instructions 112 are stored in the memory for execution on processor 140 to configure the processor to operate as an analysis engine 150, which provides various functions and operations on the data sets. For example, analysis engine 150 includes a module for data set association 152 to associate the genomic data set and the transcriptomic data set using the mutation (e.g., pairing or otherwise associating data sets with mutations in common position in the genome). Analysis engine may further include a mutation identification module 154 to identify the type of mutation (e.g., as a silent or nonsense mutation), a position identification module 156 to identify the position of the mutation within a gene or transcript, and an expression level identification module 158 that identifies that expression level of the mutated transcript (e.g., relative to a matched non-mutated transcript of the same patient). Upon identification of the mutation as a nonsense mutation, the position of the mutation is identified (e.g., as being located within the 3'-end portion of the gene) and the expression level of the gene is identified. Finally, the identified position and expression level are then used to update an omics record in the omics database 160.

Genomic data sets contemplated herein may include various information and may be formatted in a variety of ways. Therefore, suitable genomic data sets may include raw data from sequencing device or raw data storage device. Of course, it should as ne appreciated that the raw data may be preprocessed in several ways. For example, raw data may be preprocessed for improved data transmission (e.g., as described in PCT/US 14/65562) and/or formatted to facilitate downstream processing. Particularly preferred formats include BAM, SAM, and FASTA format. Where raw data or preprocessed data are provided, a data set generator may convert such data into suitable formats as noted above. In some aspects, the genomic data set is a data set that includes matched DNA sequence information for both diseased tissue and healthy tissue. While the particular sequence length in such data sets is not limiting to the inventive subject matter, it should be noted that the data set may include alignments of relatively small segments (e.g., 30 up to 100, 30 up to 300, 30 up to 500, 30 up to 700, etc.), or longer segments (e.g., 1 kb up to 10 kb, 10 kb up to 100 kb, 100 kb up to 500 kb, 500 kb up to 2 mb, 2 mb to 10 mb, etc.). In other aspects, the genomic data set is a differential sequence object, typically obtained from a synchronous and incremental alignment of BAM files as discussed in US20120059670 and US20120066001. Especially contemplated differential sequence objects will include an identification of a mutation (e.g., transition, transversion, deletion, insertion, rearrangement, etc.), typically with respect to a specific location in the genome or exome (e.g., with respect to base position on a chromosome, location within a specific gene, location within a specific exon, etc.), wherein the mutation is relative to a matched corresponding sample from the same patient (e.g., mutation is diseased tissue versus corresponding healthy tissue of same donor). It should further be recognized that the genomic data set may be generated from numerous source materials, and preferred source materials include whole genome sequences and exome enriched genome sequences (or exome sequences calculated in silico). Regardless of the source material, contemplated genomic data sets will include at least one, and more typically at least two of sequence information, location information, gene information, reference information to a reference genome, copy numbers, read support, and quality score. Genomic data set will preferably include such information for matched sequences, i.e., for a sequence of the diseased tissue and the corresponding sequence of the healthy tissue.

Viewed from a different perspective, a genomic data set will provide specific differential information with respect to differences of DNA sequences obtained from healthy and diseased tissue of the same patient.

Similarly, it is contemplated that the transcriptomic data set may vary considerably, and may include raw data from a sequencing device or a raw data storage device. As before, such data may be preprocessed for grouping as described in PCT/US14/65562 or formatted to facilitate downstream processing. Particularly preferred formats include BAM, SAM, and FASTA format. Where raw data or preprocessed data are provided, a data set generator may convert such data into suitable formats as noted above. In some aspects, the transcriptomic data set is a data set that includes matched RNA sequence information for both diseased tissue and healthy tissue. While the particular sequence length in such data sets is not limiting to the inventive subject matter, it should be noted that the data set may include alignments of relatively small segments (e.g., 30 up to 100, 30 up to 300, 30 up to 500, 30 up to 700, etc.). or longer segments (e.g., 1 kb up to 5 kb, 5 kb up to 20 kb, 20 kb up to 100 kb, etc.). In other aspects, the genomic data set is a differential sequence object, typically obtained from a synchronous and incremental alignment of BAM files as discussed in US20120059670 and US20120066001. As above, especially contemplated differential sequence objects will include an identification of a mutation (e.g., transition, transversion, deletion, insertion, rearrangement, etc.), typically with respect to a specific location in the RNA, mRNA, or primary RNA transcript (e.g., with respect to base position on a chromosome or primary transcript, location within a specific gene, location within a specific exon, specific splice variant, etc.), wherein the mutation is relative to a matched corresponding sample from the same patient (e.g., mutation is diseased tissue versus corresponding healthy tissue of same donor). Transcriptomic data set may be generated from numerous source materials, preferred material is (preferably reverse transcribed) mRNA and primary transcripts (hn-RNA). RNA sequence information is obtained from reverse transcribed polyA$^+$-RNA, which is in turn obtained from a tumor sample and a matched normal (healthy) sample of the same patient. In addition, it should be noted that the same patient sample may also be used for DNA analysis as well as tissue or cell based proteomic analysis. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Regardless of the material, transcriptomic data set will include at least sequence information, location information, gene information, reference information to a reference genome, transcription level, read support, and/or quality score, etc. Moreover, the transcriptomic data set will typically include such information for matched sequences, i.e., for a sequence of the diseased tissue and the corresponding sequence of the healthy tissue of the same patient.

In still further contemplated aspects, the genomic data set and the transcriptomic data set can be combined into a single data set that includes DNA and RNA sequence information of the diseased tissue and a corresponding healthy tissue (typically from same donor/patient). In such case it is especially preferred that the combined omic data set is a prepared from the respective DNA and RNA BAM files in a location synchronized incremental alignment that produces a differential sequence object containing the differences for a particular sequence or gene with respect to at least sequence, mutation location, copy number, expression level, etc. for both DNA and RNA sequences of diseased and matched healthy tissues.

With respect to especially contemplated aspects of generating the genomic and/or transcriptomic data sets it is therefore contemplated that simultaneous analysis of tumor and matched RNA is preferably performed using an algorithm and methods as described in US 2012/0059670 and US 2012/0066001, which are incorporated by reference herein. In addition, it should be appreciated that tumor and matched DNA analysis may be performed using the same patient sample, thus providing genomic and transcriptomic (RNomic) data for the same patient and from the same sample. These data can then be further processed to obtain pathway relevant data using systems and methods as described in WO/2011/139345 and WO/2013/062505, also incorporated by reference herein. Thus, it should be noted that a single pathway analysis for a patient may be performed form a single patient sample and matched control, which will significantly improve and refine analytic data as compared to single omics analysis. In addition, the same analytic methods may further be refined with additional omic data (e.g., proteomic data) and/or patient specific history data (e.g., prior omics data, current or past pharmaceutical treatment, etc.). In addition, it should be noted that further data may also be obtained from various other sources, including various commercial sequencing centers and/or academic institutions. On the basis of these data, more accurate diagnoses or predictions can be made, as well as treatment options that are based on refined pathway analyses.

With respect to the corresponding tissues used in the systems and methods herein, it is generally contemplated that at least two distinct tissues are employed in the generation of the genomic and transcriptomic data sets. For example, where the first tissue is a diseased tissue (e.g., neoplastic, cancerous, infected, traumatized, etc.), the second tissue is a non-diseased tissue, which may or may not be derived from the same organ or tissue type. Alternatively, or additionally, first and second tissues may be both diseased and from a different point in time to so identify or characterize treatment effect, disease progression or reversal, etc.

Contemplated analysis engines will typically include a module for data set association that associates the genomic data set and the transcriptomic data set using the mutation (e.g., pairing or otherwise associating genomic and transcriptomic data sets with mutations in common position in the genome). Viewed from another perspective, genomic and transcriptomic data sets are aligned such that corresponding sequences or locations can be compared between the genomic data set and the transcriptomic data set and that the genomic and transcriptomic data sets include a common mutation. Thus, the association module lines up DNA information with the corresponding RNA information, typically for both the diseased tissue and the healthy tissue, or where a differential sequence object is provided, the association module lines up corresponding mutations in the differential sequence objects between the DNA of the diseased and healthy tissue with the differential sequence object between the corresponding RNA sequences of diseased and healthy tissues. In that way, it should be appreciated that all relevant information (e.g., type of mutation, sequence information of mutation, copy number information, transcription level information, etc.) with respect to a specific mutation at a specific location can be associated for further analysis.

Contemplated analysis engines will further include a module for mutation identification that identifies and/or classifies any mutations in the genomic and transcriptomic data sets, wherein identification and classification include identification of at least a nonsense mutation, and further identification of a missense and/or silent mutation. Of course it should be noted that additional information associated with the mutations may also be identified and/or classified, and typical examples of such additional information includes frame shift information, translocation information, alternative splicing information, rearrangement information, etc.

In further contemplated aspects of the inventive subject matter, the analysis engine will include a module that is configured to identify a position of the identified mutation within the gene affected by the mutation, and a further module that is configured to identify the expression (transcription) level of the gene carrying the mutation (typically using the information provided in the transcriptomics data set). For example, and as described in more detail below, position identification may be relevant in assessing significance of a mutation where the mutation is a nonsense mutation. Therefore, position information may include identification or confirmation of a mutation as being located within the 3'-end portion of a gene and/or transcript. As used herein, the term "within the 3'-end portion" refers to a position being with the 3'-terminal 50%, or the 3'-terminal 40%, or the 3'-terminal 30%, or the 3'-terminal 20%, or the 3'-terminal 10% of a sequence. Viewed from a different perspective, the term "within the 3'-end portion" may also refer to the 3'-terminal exon, or the last two 3'-terminal exons, or the last three 3'-terminal exons.

Based on the inventors' findings below, an omics record for the patient may be updated or generated based on the information obtained from the coordinated genomics/transcriptomics analysis. For example, the omics record may be updated where the mutation in the genome and transcriptome is a nonsense mutation in a gene, and where the transcription level of that gene is greater than the transcription level of the corresponding unmutated gene. Suitable omics databases will typically include omics records form a plurality of patients and may be used to store omics raw or processed data, genomic data sets, transcriptomic data sets, differential sequence objects, BAM files, etc.

Consequently, in view of the above and examples to follow, it should be recognized that contemplated systems and methods will readily provide a new avenue for identification of potential molecular markers for treatment and diagnostics for cancers based on genomic and transcriptomic information. Viewed from a different perspective, the inventors contemplate that by patient specific identification of genomic mutations and corresponding RNA expression levels, highly transcribed mutated RNA (and especially nonsense mutated RNA) may be confirmed and/or used as a diagnostic tool for the presence, treatment or prevention of various cancers.

For example, as is exemplarily shown in Table 1, TCGA provides for 13 different types of cancers a significant number of exon pair data (total of >5,000) as well as corresponding RNA sequences (total of >3,900). Using these data, numerous DNA/matched RNA analyses were performed as is described in more detail below.

TABLE 1

| Cancer | #Samples w/exome pairs | #Samples w/RNA-Seq |
|---|---|---|
| LUAD | 464 | 386 |
| LUSC | 474 | 375 |

TABLE 1-continued

| Cancer | #Samples w/exome pairs | #Samples w/RNA-Seq |
|---|---|---|
| GBM | 343 | 39 |
| LAML | 122 | 1 |
| KIRC | 320 | 323 |
| COLO | 333 | 69 |
| STAD | 279 | 275 |
| BRCA | 932 | 927 |
| UCEC | 307 | 288 |
| SKCM | 315 | 272 |
| OV | 317 | 197 |
| THCA | 442 | 445 |
| HNSC | 359 | 315 |
| Total | 5,007 | 3,912 |

Figure 2:
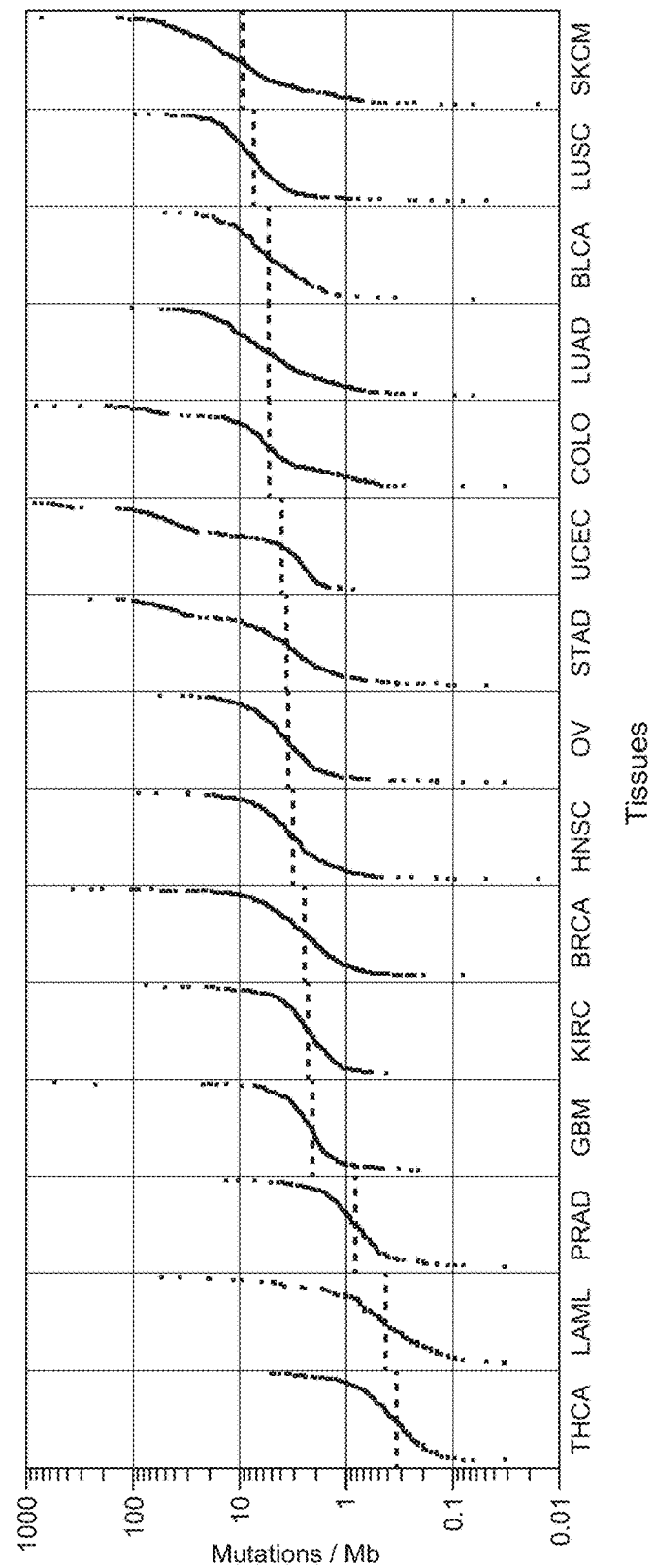
FIG. 2 is a graph illustrating somatic mutational profiles for selected cancers.
Figures 1, 3:
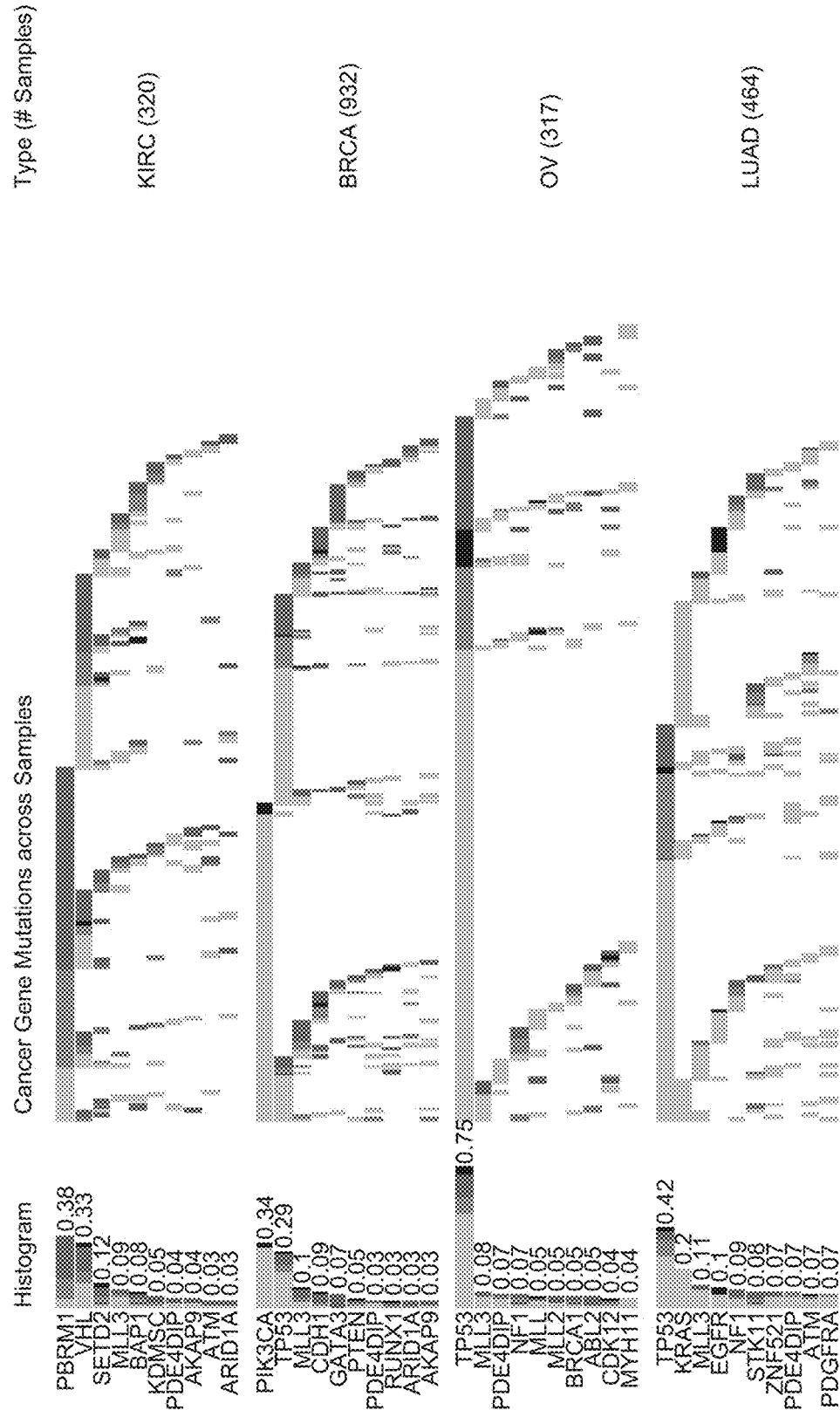
FIG. 3 is a graph providing a detail view for mutation types and occurrences in selected genes for particular cancers.
Figures 2, 3:
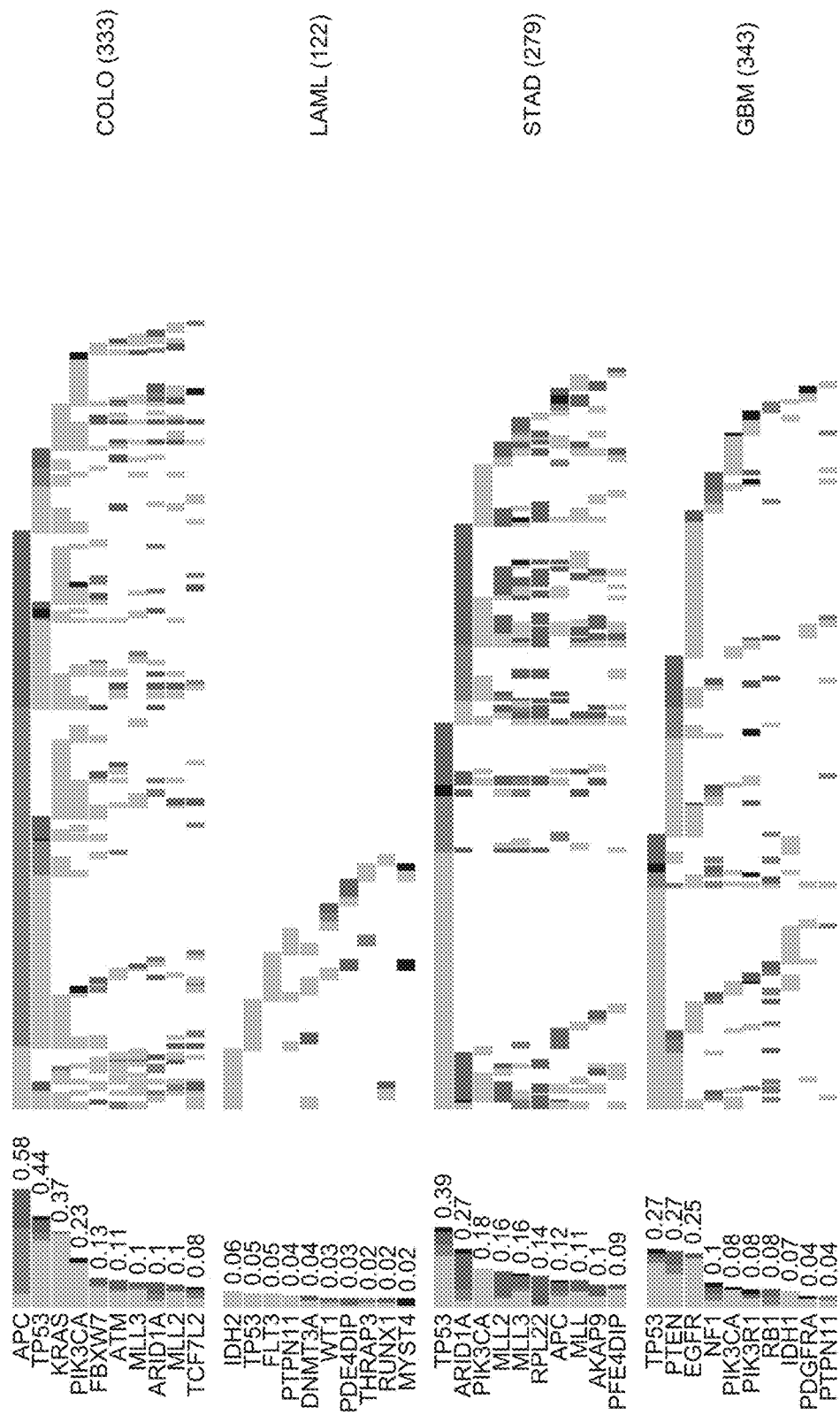
Figure 3:
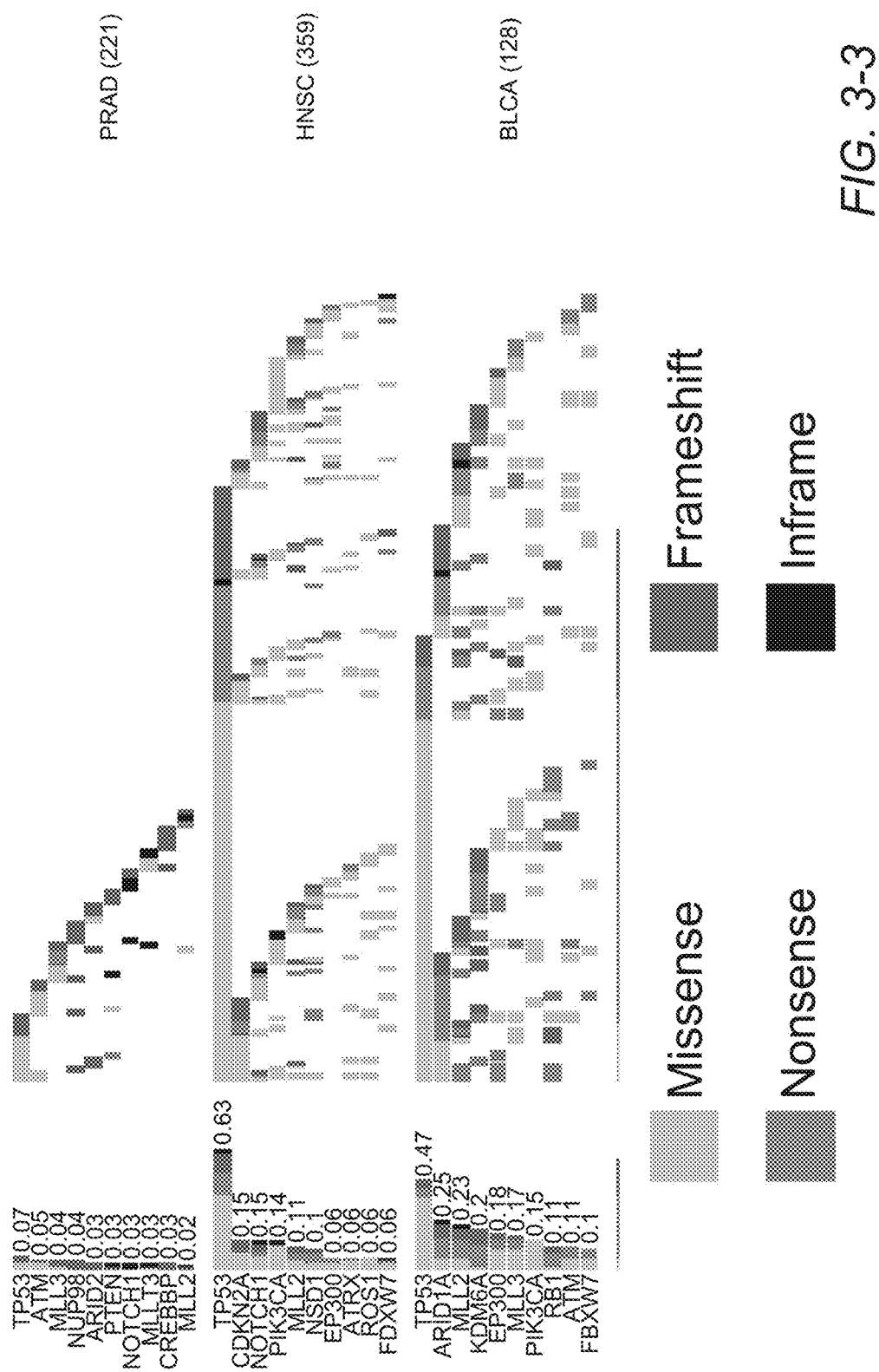

Further analysis of the data from the TCGA provided various somatic mutational profiles for the cancers listed in Table 1 above, and the mutation frequency per Mb is exemplarily depicted in FIG. 2. As can be seen, most mutational frequencies are within one order of magnitude and have substantially similar sigmoidal distribution pattern. FIG. 3 exemplarily provides a more detailed view of the somatic mutational profiles for selected genes within the cancer type, listing the most affected genes per tumor type with respective mutation types (missense, nonsense, frame shift, in-frame) in a histogram. Moreover, FIG. 3 also illustrates the potential associations of mutation types in a single tumor type among the most affected genes. As can be seen, no substantial bias or specific association is seen across all tumor types.

With respect to transcription the inventors noted that, as can be taken form Table 2 below, a substantial number (>80%) of mutations in the genome were also expressed/found in the transcriptome, with no apparent substantial bias for or against a particular type (e.g., silent, missense, nonsense) of mutation. As can be taken from Table 2, the overall fraction of nonsense mutations was approximately 5% of all detected mutations, the overall fraction of silent mutations was approximately 28% of all detected mutations, and the overall fraction of missense mutations was approximately 67% of all detected mutations. As used herein, the term "detected" means that at least one read supporting mutant allele was found in RNA-Seq data, while the term "absent" means that no mutant allele was detected in RNA-Seq data. Furthermore, the data in Table 2 only considered mutations with confidence>=20 with at least 20 reads covering position in RNA-Seq.

TABLE 2

| Variant Type | Detected | Absent | % Detected |
|---|---|---|---|
| Silent | 57,125 | 12,121 | 82.5% |
| Missense | 137,807 | 24,507 | 84.9% |
| Nonsense | 9,548 | 2,348 | 80.3% |

Figures 3, 4:
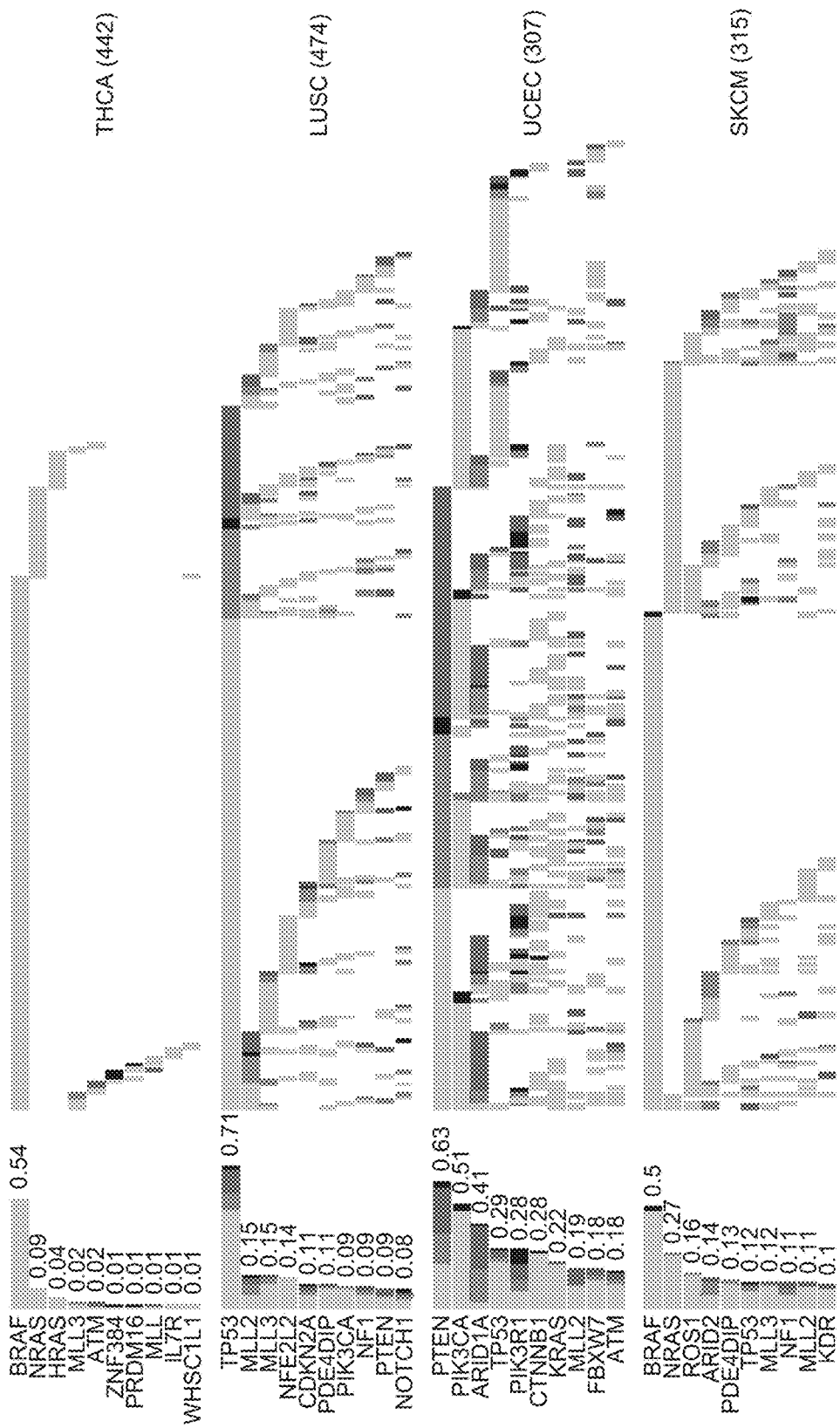
FIG. 4 is a scatter plot depicting mutant allele fractions (DNA vs. RNA) for silent mutations vis-à-vis all mutations.
Figure 4:
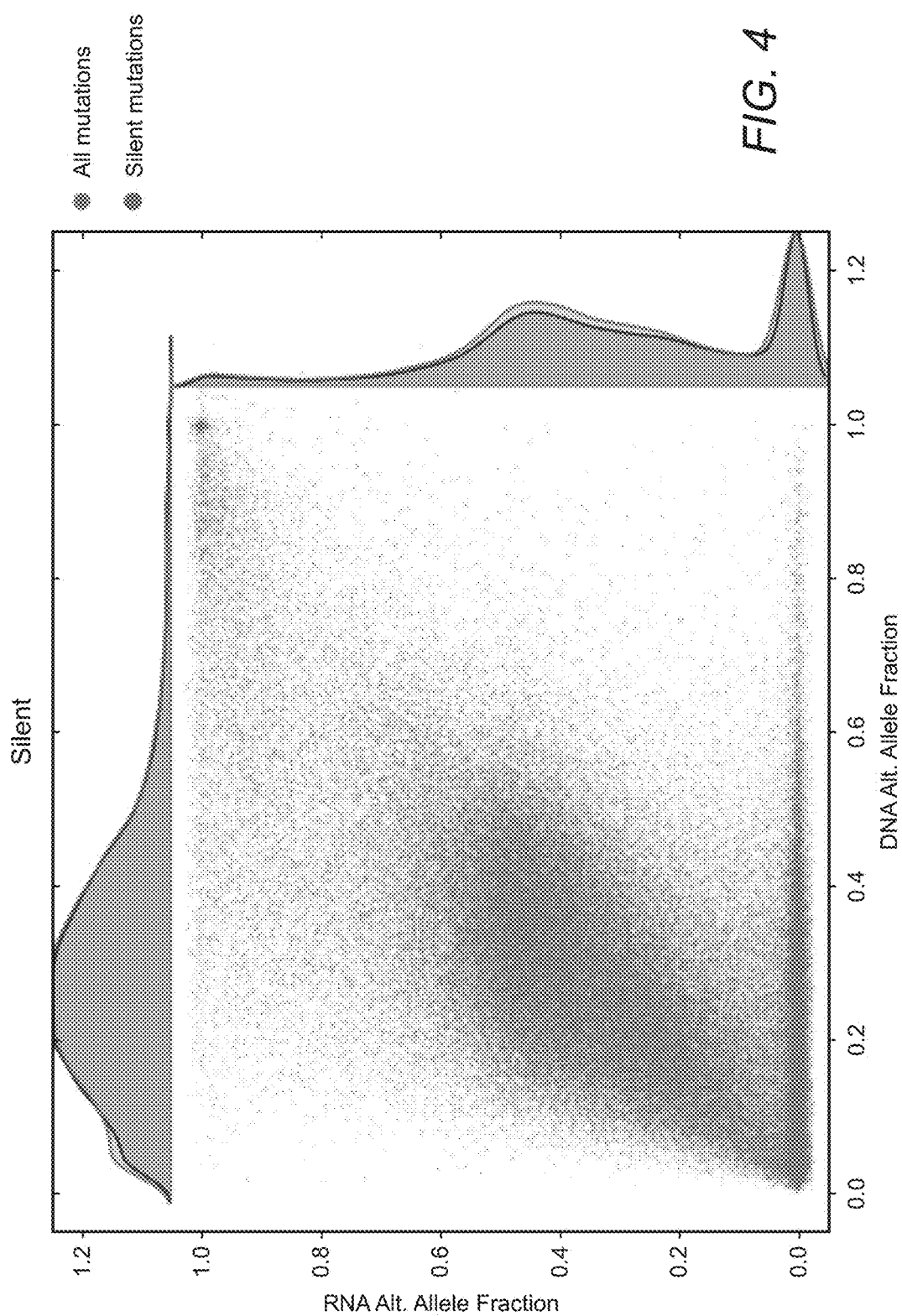
Figure 5:
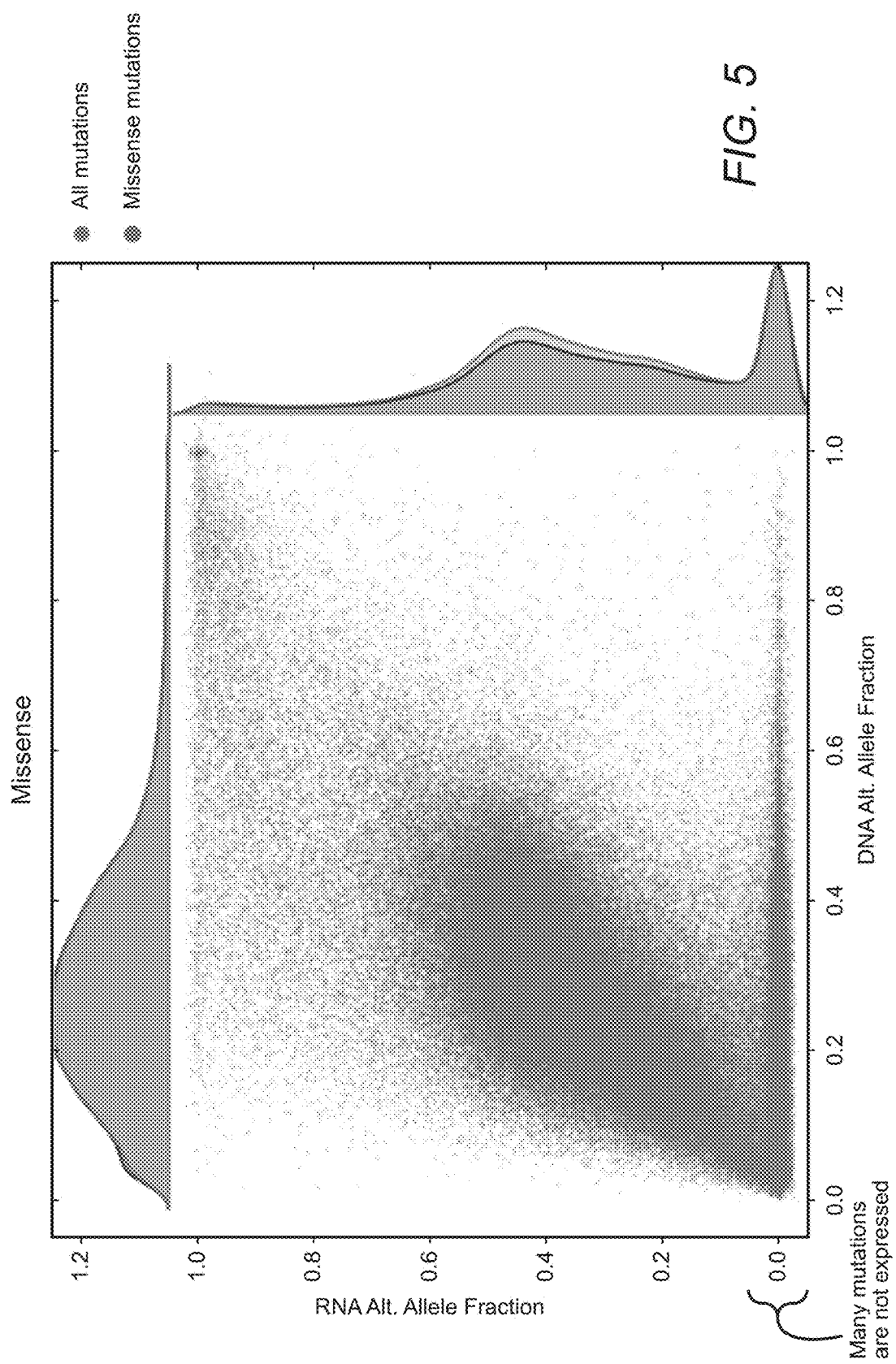
FIG. 5 is a scatter plot depicting mutant allele fractions (DNA vs. RNA) for missense mutations vis-à-vis all mutations.
Figure 6:
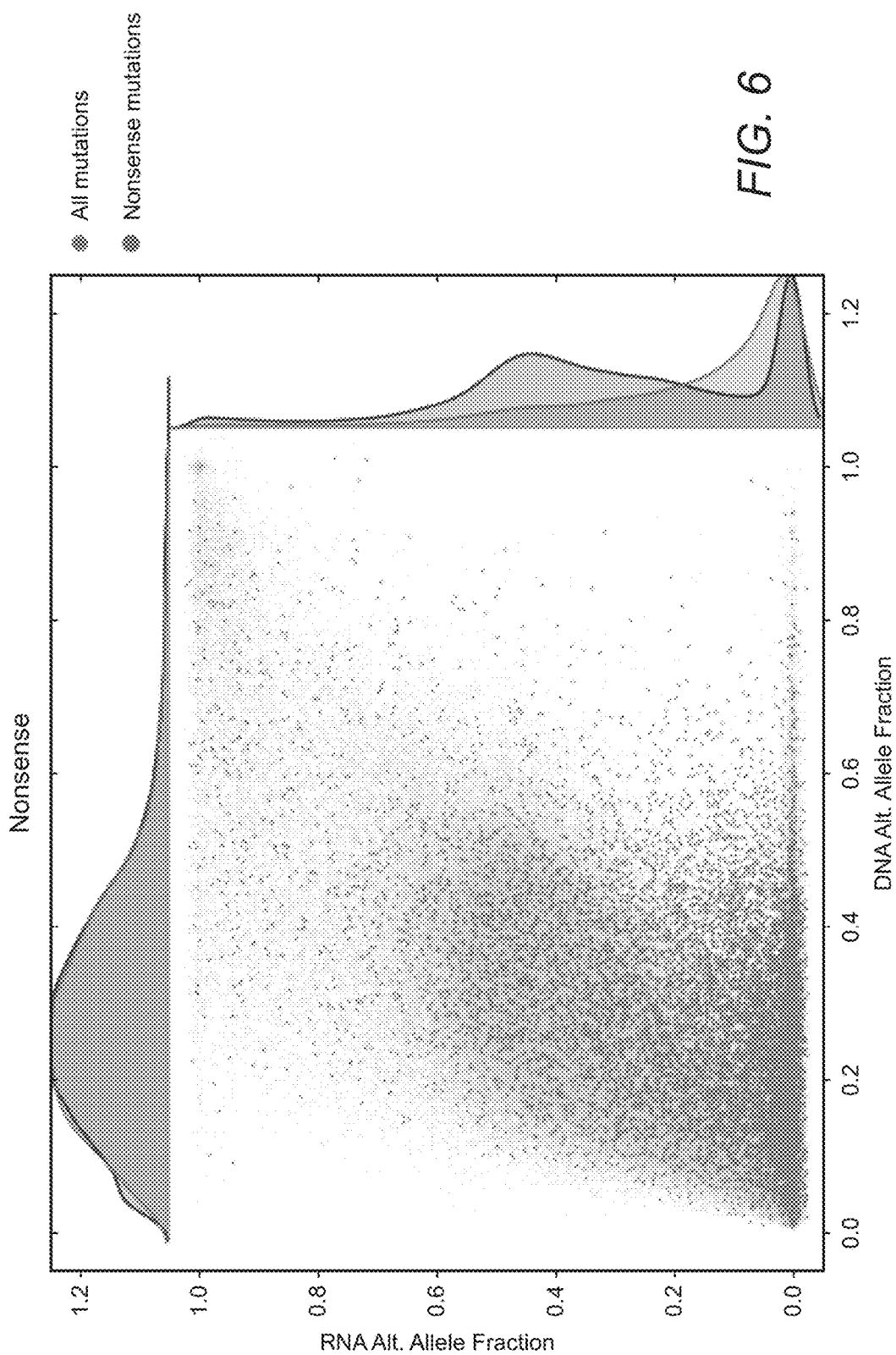
FIG. 6 is a scatter plot depicting mutant allele fractions (DNA vs. RNA) for nonsense mutations vis-à-vis all mutations.
Figure 7:
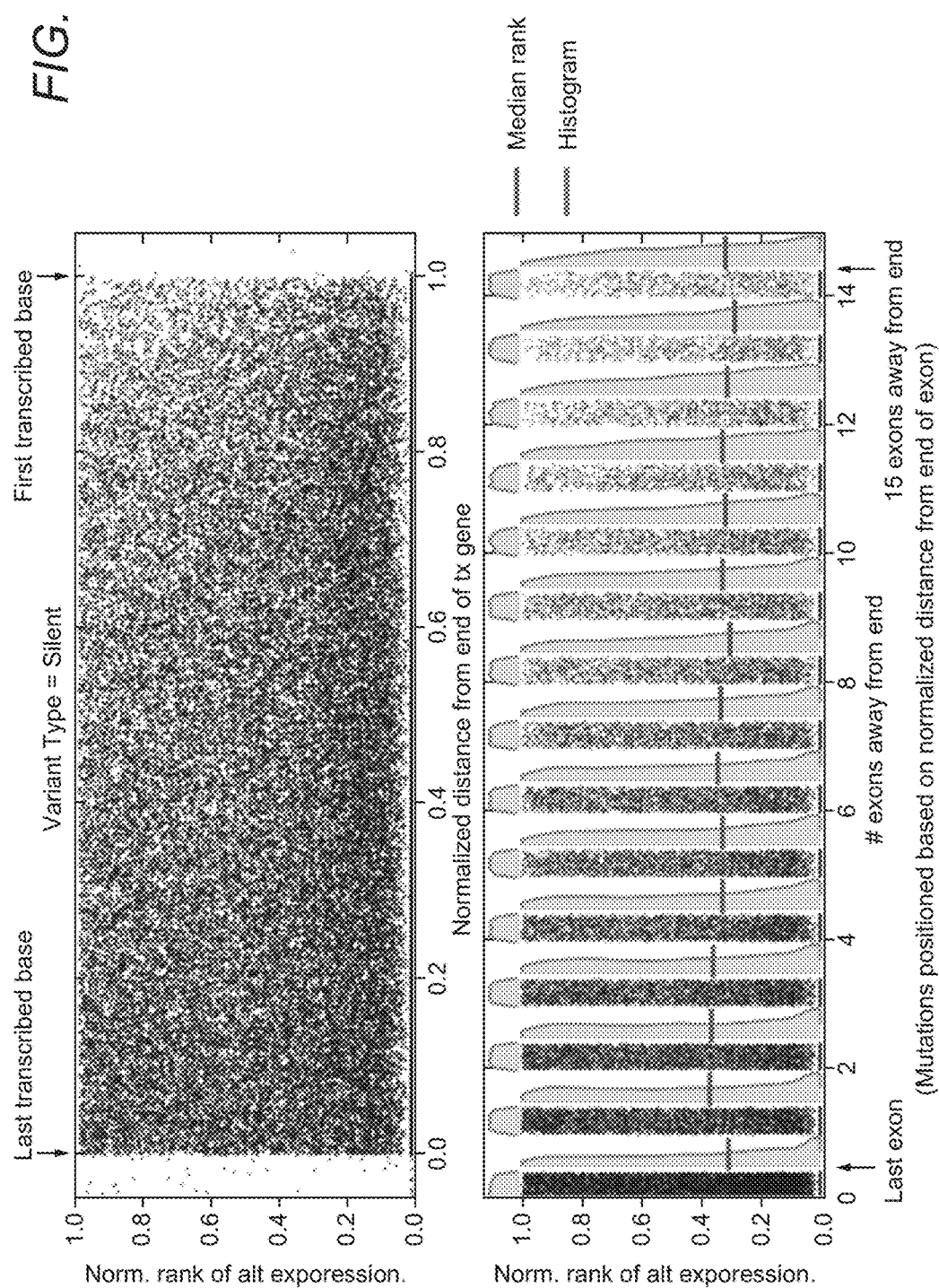
FIG. 7 is a graph illustrating expression levels as a function of mutation position for silent mutations.
Figure 8:
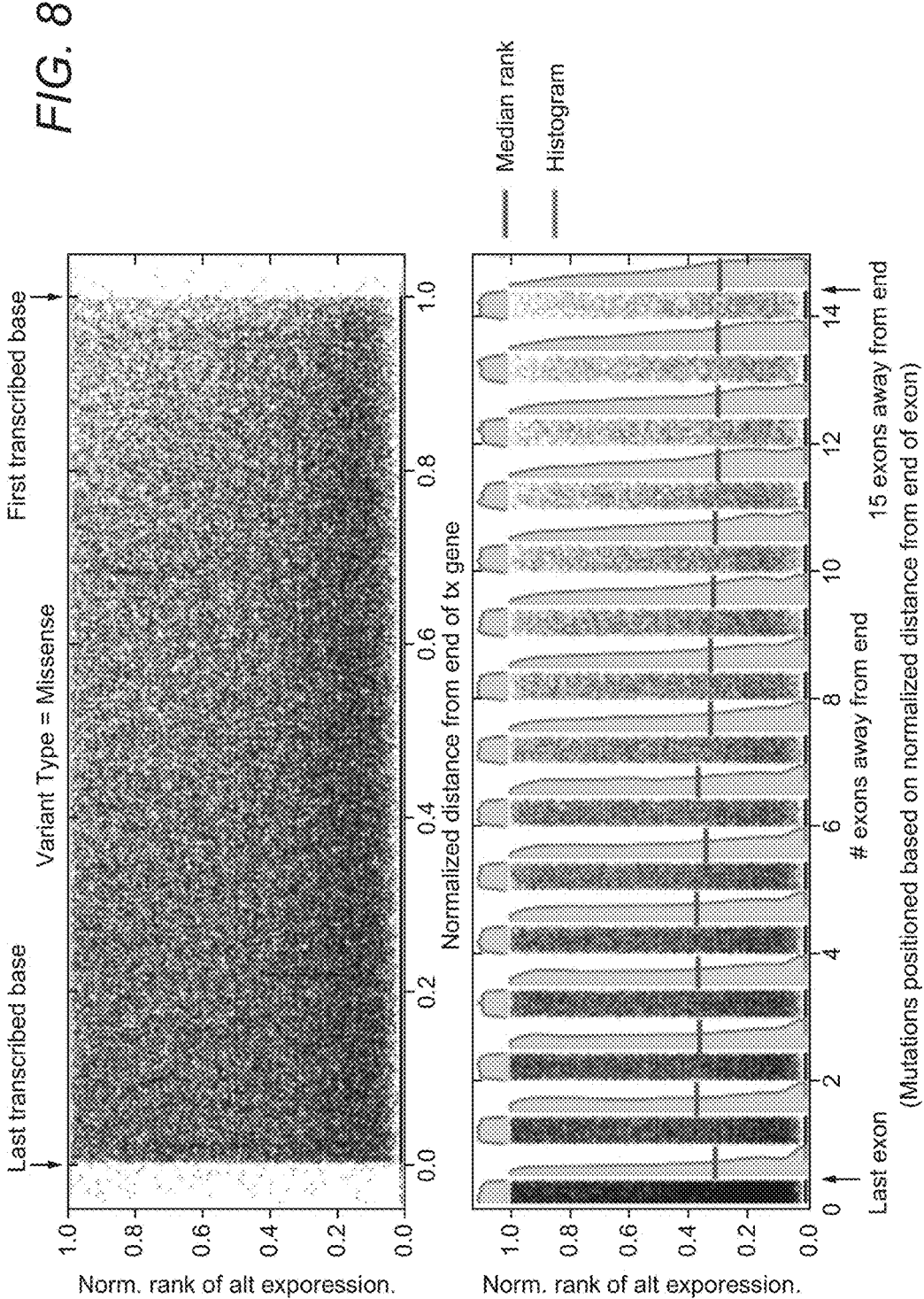
FIG. 8 is a graph illustrating expression levels as a function of mutation position for missense mutations.
Figure 9:
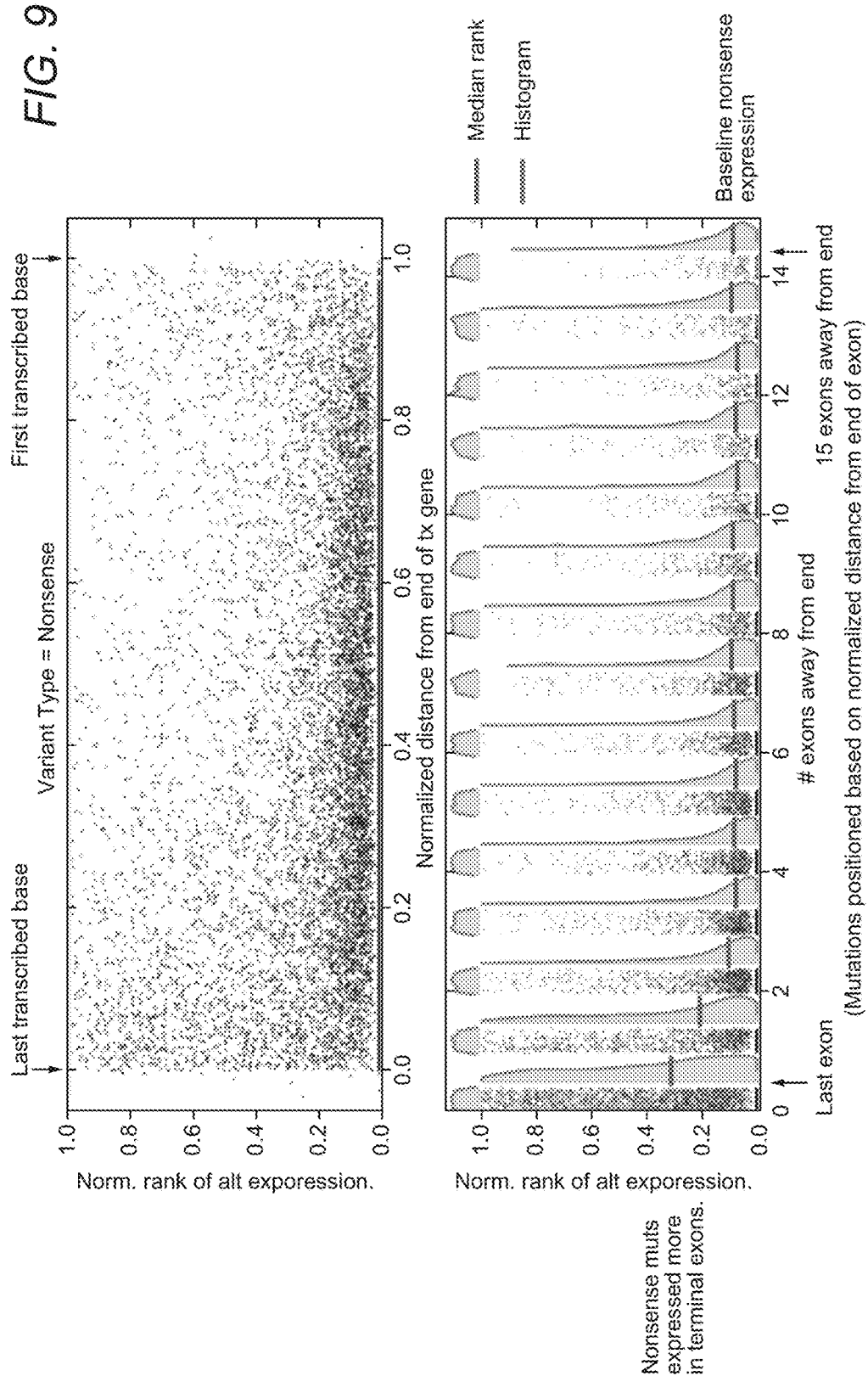
FIG. 9 is a graph illustrating expression levels as a function of mutation position for nonsense mutations.
Figure 10:
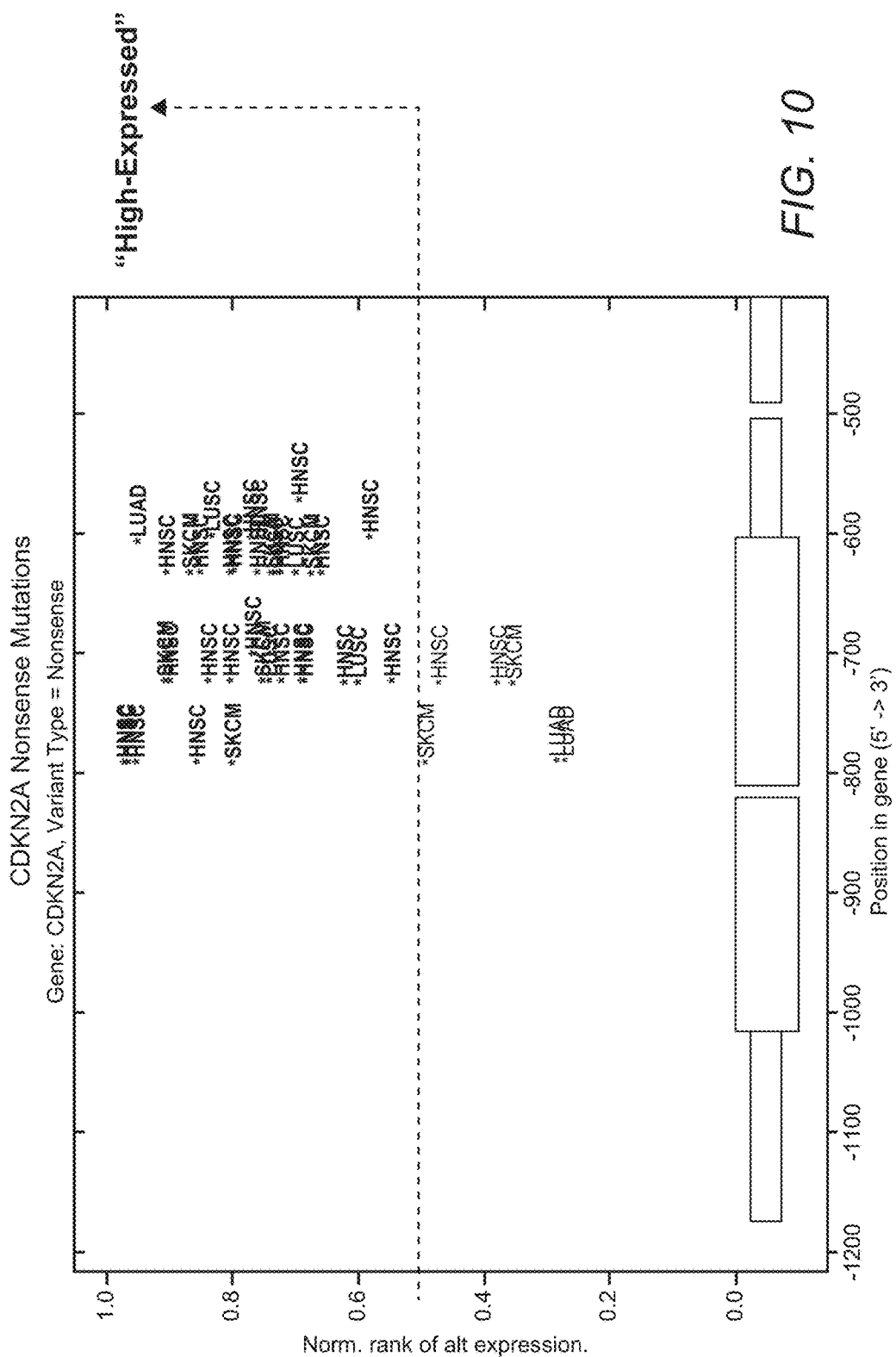
FIG. 10 is a graph plotting highly expressed RNA with nonsense mutations against position of the nonsense mutation in the CDKN2A gene.
Figure 11:
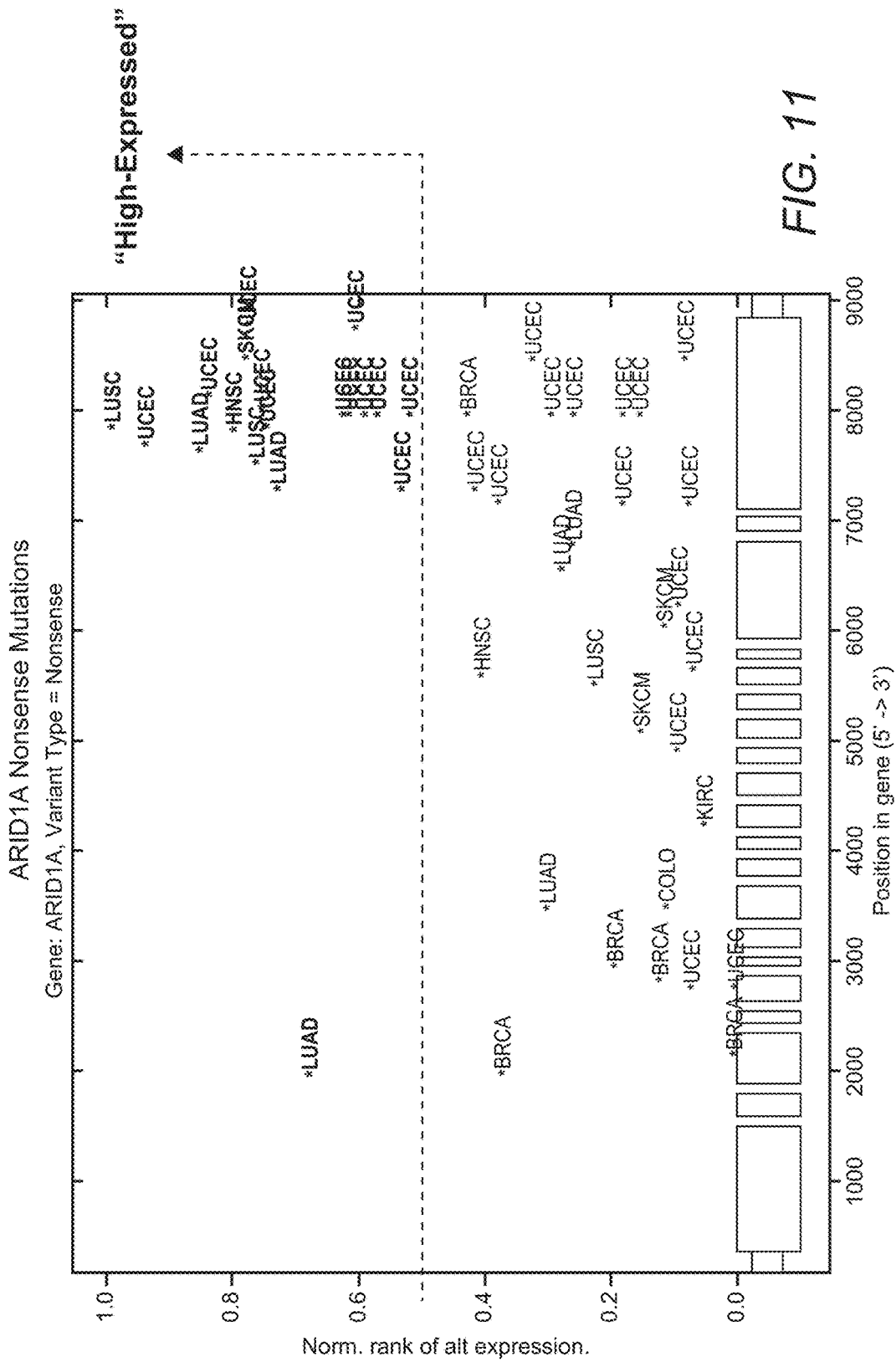
FIG. 11 is a graph plotting highly expressed RNA with nonsense mutations against position of the nonsense mutation in the ARID1A gene.
Figure 12:
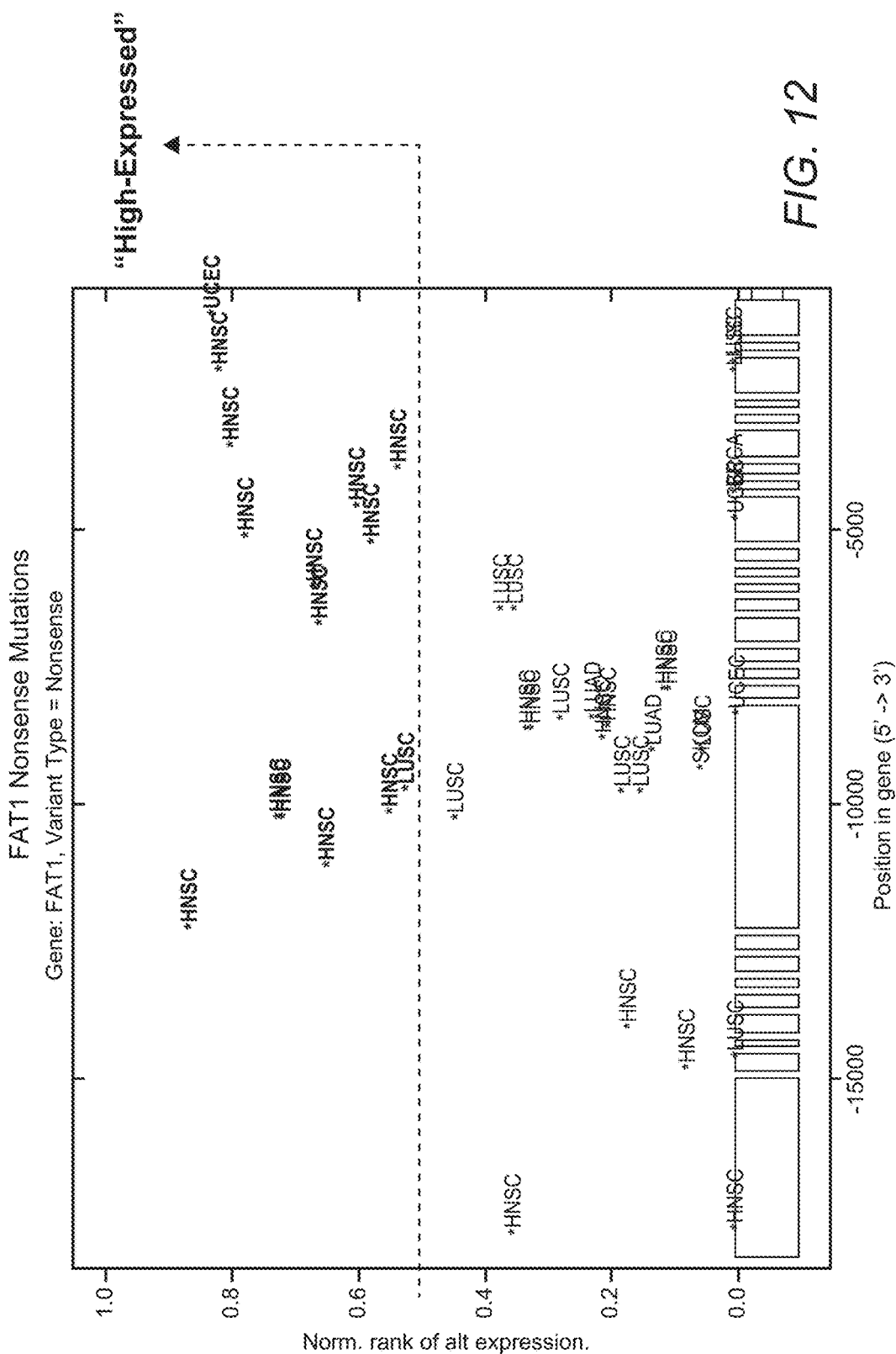
FIG. 12 is a graph plotting highly expressed RNA with nonsense mutations against position of the nonsense mutation in the FAT1 gene.
Figure 13:
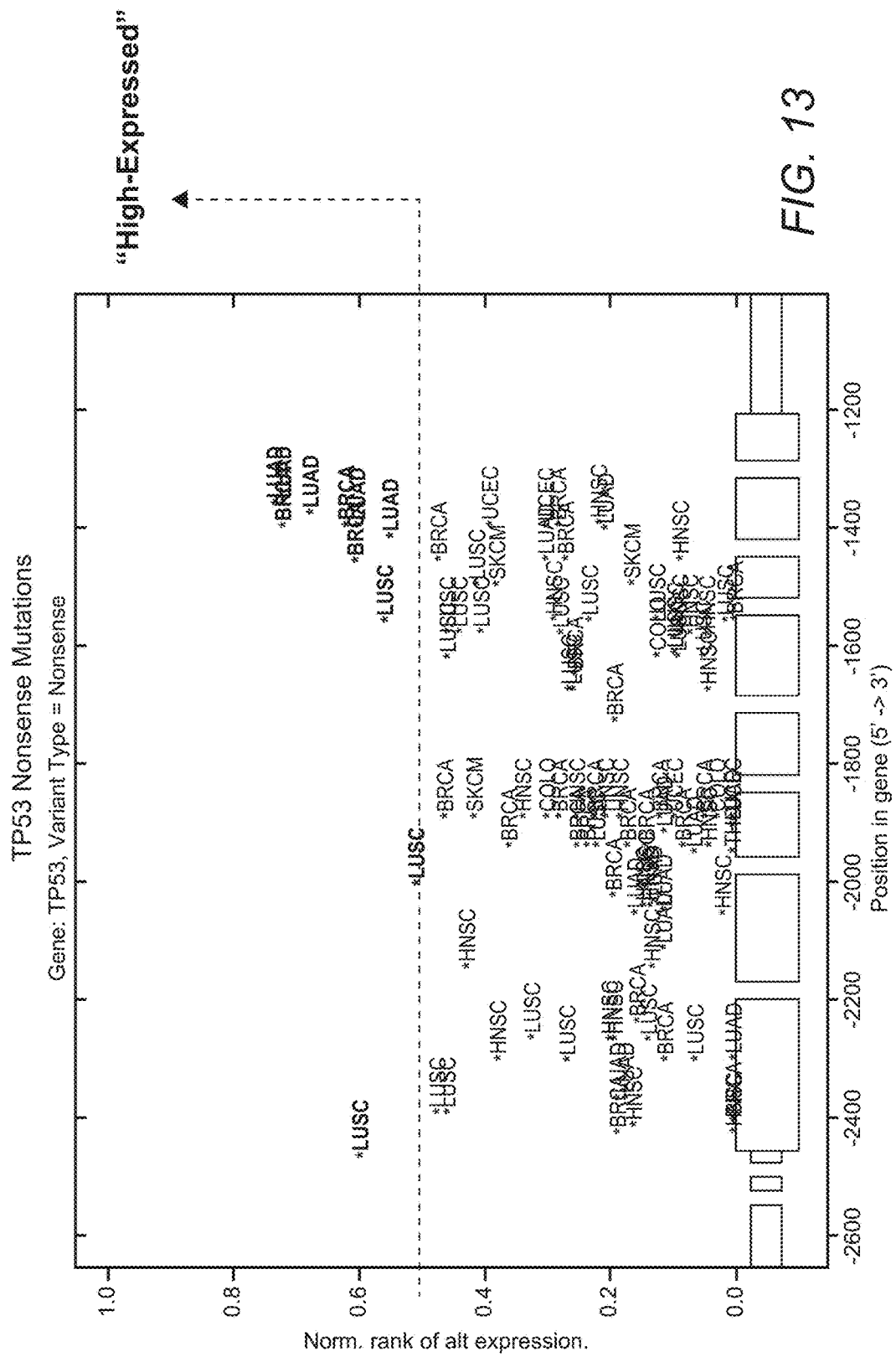
FIG. 13 is a graph plotting highly expressed RNA with nonsense mutations against position of the nonsense mutation in the TP53 gene.
Figure 14:
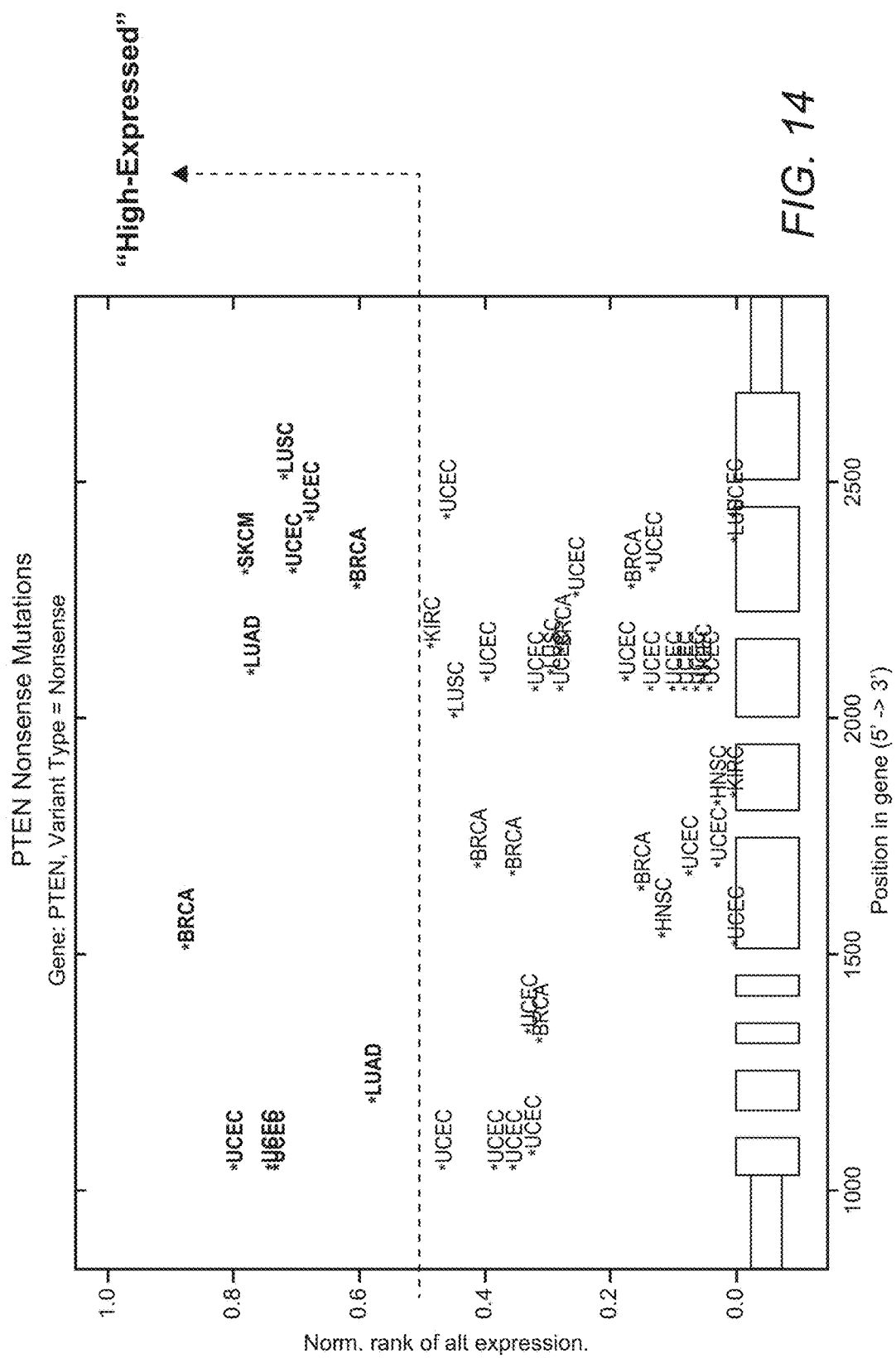
FIG. 14 is a graph plotting highly expressed RNA with nonsense mutations against position of the nonsense mutation in the PTEN gene.

FIGS. 4-6 provide a genome-wide analysis of the DNA Mutant Allele Fraction (MAF) vs. RNA for silent mutations (FIG. 4), for missense mutations (FIG. 5), and nonsense mutations (FIG. 6), indicating no significant bias in transcription in silent and missense mutations as compared to all mutations. However, it should be noted that as is reflected in Table 2 above, a portion of mutated DNA is not transcribed into RNA as is also specifically indicated in FIG. 5. Notably, FIG. 6 depicts a moderate bias towards lower/no transcription of mutated DNA, which led the inventors to analyze possible mechanisms for such apparent bias. Surprisingly, when the transcription rate was plotted against the location of the mutation for each of the mutation types, the inventors noted that a similar lack of substantial bias was observed for silent and missense mutations as can be seen from FIGS. 7-9, but in the case of nonsense mutations, as is shown in FIG. 9, nonsense mutations are significantly higher expressed within the 3'-end portion of the gene, and especially the last two terminal exons.

Upon closer investigation, and in contrast to the apparent lack in bias of the mutation type as it relates to genome-wide transcription, several selected genes in the cancer samples did show a distinct highly expressed pattern where the gene had a nonsense mutation as is listed in Table 3 below.

TABLE 3

| Gene | Total | Cancer Breakdown |
|---|---|---|
| CDKN2A | 39 | 25 HNSC, 7 LUSC, 6 SKCM, 1 LUAD |
| ARID1A | 23 | 14 UCEC, 4 LUSC, 3 LUAD, 1 SKCM, 1 HNSC |
| FAT1 | 17 | 15 HNSC, 1 UCEC, 1 LUSC |
| TP53 | 13 | 6 LUAD, 4 LUSC, 3 BRCA |
| PTEN | 12 | 6 UOEC, 2 LUAD, 2 BRCA, 1 SKCM, 1 LUSO |
| AHNAK | 6 | 5 LUSC, 1 UCEC |
| SRRM2 | 5 | 1 SKCM, 1 LUSC1 1 HNSC, 1 COLO |
| RASA1 | 5 | 4 LUSO, 1 UCEC |
| PIK3R1 | 5 | 5 UCEC |
| MRPL32 | 5 | 3 LUSC, 2 UCEC |

Interestingly, a large proportion of these mutated genes were associated with squamous cell malignancies. FIGS. 10-14 exemplarily depict an analysis of selected genes for which transcription rates were above normal and where such high expression was associated with a nonsense mutation that was located in the 3-terminal portion of the gene/transcript. In these Figures, the dotted line indicates the threshold for a highly expressed gene, (i.e., mutant read support ranks above 50% of reference). Based on these data, it should be appreciated that the above mutated genes will readily serve as a prognostic or diagnostic maker for the associated cancers. Consequently, it should be appreciated that highly transcribed nonsense mutations (particularly where the mutation is located in a 3-terminal portion of a gene) may be used in systems and methods of detecting molecular markers for diagnosis and treatment of various cancers.

Thus, specific embodiments and applications of methods of omics analysis have been disclosed. It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer assisted method of treating a patient having cancer, comprising:

obtaining or generating a genomic data set and a transcriptomic data set;
  wherein the genomic data set includes DNA sequence data that is representative of a mutation in at least one tumor-associated gene of a diseased tissue of the patient, and wherein the mutation is relative to a normal tissue of the patient;
  wherein the transcriptomic data set includes 1) RNA sequence data that is representative of the mutation in the at least one tumor-associated gene and 2) RNA expression level data of the at least one tumor-associated gene of the diseased tissue of the patient, and wherein the mutation and expression level are relative to the normal tissue of the patient;
using a sequence analysis engine to:
  (a) associate the transcriptomic data set with the genomic data set using the mutation;
  (b) identify the mutation as a nonsense mutation, and upon identification of the mutation as nonsense mutation to:
  (c) identify a position of the mutation within the 3'-end portion of the at least one gene; and
  (d) identify the expression level of the at least one gene; and
treating the patient by targeting the at least one gene when the identified position is a position in the 3-terminal portion of the gene and the identified expression level is above an expression level relative to the normal tissue.

2. The method of claim 1 further comprising informationally coupling a sequence database or sequencing device with the sequence analysis engine, and using the sequence analysis engine to generate the transcriptomic data set and the genomic data set.

3. The method of claim 1 wherein the transcriptomic data set and the genomic data set are differential sequence objects.

4. The method of claim 1 wherein the diseased tissue is a cancerous tissue.

5. The method of claim 1 wherein the transcriptomic data set is associated with the genomic data set when the mutation is in the same position.

6. The method of claim 1 wherein the transcriptomic data are obtained from cDNA or polyA$^+$-RNA.

7. The method of claim 1 wherein the gene is selected from the group consisting of CDKN2A, ARID1A, FAT1, TP53, PTEN, AHNAK, SRRM2, RASA1, PIK3R1, and MRPL32.

8. The method of claim 1, further comprising updating or generating, by the sequence analysis engine, the omics record using the position of the mutation and the expression level when the identified position is the position in the 3-terminal portion of the gene and the identified expression level is above the expression level relative to the normal tissue.

* * * * *